United States Patent [19]

Coelho et al.

[11] Patent Number: 5,103,651
[45] Date of Patent: Apr. 14, 1992

[54] PLASMA STORAGE FREEZER AND THERMAL TRANSPORT DEVICE

[75] Inventors: Philip H. Coelho; Terry Wolf, both of Rancho Cordova, Calif.

[73] Assignee: Instacool Inc of North America, Sacramento, Calif.

[21] Appl. No.: 575,836

[22] Filed: Aug. 31, 1990

[51] Int. Cl.⁵ .............................................. F25L 5/14
[52] U.S. Cl. .................... 62/341; 62/457.2; 62/430; 62/530; 220/444; 220/461
[58] Field of Search .................. 62/457.1, 457.2, 457.9, 62/457.7, 529, 530, 430, 341; 220/444, 453, 23.86, 459, 461

[56] References Cited

U.S. PATENT DOCUMENTS

| | | | |
|---|---|---|---|
| 2,034,472 | 3/1936 | Kesslinger | 62/457.1 |
| 4,145,895 | 3/1979 | Hjertstrand et al. | 62/529 |
| 4,251,995 | 2/1981 | Pert et al. | 62/341 |
| 4,470,264 | 9/1984 | Morris | 62/530 |
| 4,530,816 | 7/1985 | Douglas-Hamilton | 62/457.2 |
| 4,723,974 | 2/1988 | Ammerman | 62/530 |
| 4,951,482 | 8/1990 | Gilbert | 62/457.1 |
| 4,958,506 | 9/1990 | Guilhem et al. | 62/457.2 |

Primary Examiner—Henry A. Bennet
Assistant Examiner—John Sollecito
Attorney, Agent, or Firm—Bernhard Kreten

[57] ABSTRACT

A thermal transport device having a hollow within which a plasma storage freezer is deployed. The freezer acts as a cold "battery" by having a eutectic fluid contained therewithin. The freezer is placed in a commercial, powered refrigeration unit for chilling ("charging") the eutectic fluid of the plasma storage freezer to approximately −30° C. The freezer is then deployed within the thermal transport device and sent to a remote locale for collecting blood plasma. Blood plasma is disposed between a central heat sink and lateral heat sinks of the freezer freezing the blood plasma quickly and maintaininig its initial high quality because of negligible time loss for freezing. Ultimately, the device is returned to a commercial powered refrigeration unit for ("recharging") rechilling the eutectic fluid for subsequent reuse.

24 Claims, 3 Drawing Sheets

PLASMA STORAGE FREEZER AND THERMAL TRANSPORT DEVICE

FIELD OF THE INVENTION

The following invention relates generally to an instrumentality which rapidly freezes plasma soon after it has been donated to assure that it is of the highest quality, particularly when the site of donation is remote from a commercial, powered freezing unit. The device is dimensioned to accommodate a typical day's work product capable of being produced from a team of technicians and is provided with an outer transport device that is sufficiently insulated to last the time necessary for return of the plasma to a permanent storage site having a powered freezer for subsequent use.

BACKGROUND OF THE INVENTION

Various programs and incentives exist which dictate, to a certain degree, the manner in which blood donations occur. In some cultures where blood and/or plasma is sold, donors frequently will travel to a permanent location to effect the exchange. This procedure has certain benefits in that a normal, electrically powered, commercial refrigeration system can be used to blast freeze the drawn plasma.

It is imperative that the blood plasma be frozen as soon as possible after collection in order to maintain its highest qualities. Blood plasma proteins are thermolabile and can degrade in quality from its highest level to an inferior grade quite quickly. Thus, fixed locations with permanent blast freezing capabilities can be effectively utilized to preserve the blood in its highest quality immediately after collection.

However, there is an increasing demand for plasma from individuals that are willing to donate their plasma at no charge. In order to attract these donors, the collectors must set their equipment at sites convenient to the donors, often remote from the main blood processing centers. In some cases a mobile unit, such as a large van, will be sent to remote locations and effect plasma collection when a fixed processing site is geographically inconvenient to the donor. While such large expensive vehicles, which have the beds and processing equipment onboard, can collect the blood products, they do so at a relatively high cost per liter of plasma collected and the donor is still required to leave his place of business and go to the van to donate his blood or plasma.

More often it is required to be even more convenient for the donor - that is to set up within the donor's place of work. However these locations are often up in buildings and require the lifting and handling of all the necessary equipment by the blood collection staff. An onerous job results.

The necessary equipment to collect plasma is usually transported in smaller vans to these private or public buildings which house a suitable population of workers who are willing to donate their blood or plasma, now that the location of donation site is so convenient. In both of these methods of collecting blood or plasma the cost is quite high.

Consequently, because it is especially important that such expensive blood products be collected and maintained at their highest quality, this requires refrigeration which is compact, light weight and easily transportable by one or two people. Until now, the only means available for rapid freezing in such circumstances was from the use of very expensive, expendable cryogens like $LN_2$ and $CO_2$. In addition to being costly, $LN_2$ and $CO_2$ are somewhat dangerous to handle and are so cold they embrittle the plastic bags which house the plasma. These weakened bags often break which leads to extraordinary costly wastage of precious fluids.

Other similar examples of sites where the importance of collecting high quality blood exists include within relatively undeveloped countries that have low levels of industrialization and during military maneuvers. Both describe situations where collection is most arduous.

The following patents reflect the state of the art of which applicant is aware insofar as these prior art citations appear germane to the process at hand. However, it is stipulated that none of these patents teach singly nor render obvious when considered in any conceivable combination the nexus of the instant invention as particularly claimed and described.

| INVENTOR | PATENT NO. | ISSUE DATE |
|---|---|---|
| Hjerstrand, et al. | 4,145,895 | March 27, 1979 |
| Faust, et al. | 4,194,369 | March 25, 1980 |
| Sheehan, et al. | 4,322,954 | April 6, 1982 |
| Campbell, J. H. | 4,343,158 | August 10, 1982 |
| Morris, S. D. | 4,470,264 | September 11, 1984 |
| Toledo-Pereyra, L. | 4,502,295 | March 5, 1985 |
| Van Iperen, et al. | 4,923,077 | May 8, 1990 |

The patent to Morris teaches the use of a life support apparatus for human blood and compositions thereof in which a transportable self-contained life support apparatus steadily reduces in temperature whole blood collected from donors to a predetermined temperature range which is above freezing because whole blood cannot be frozen without damaging the cells. Unlike the instant invention, no freezing is involved and as will be developed infra, no eutectic mixture is integrated into the Morris apparatus. As a result, the blood stored according to this known prior art technique is at a higher temperature than that which is attainable in the instant invention and which is much more desirable.

Similarly, the patent to Hjerstrand, et al. teaches the use of an apparatus for storing goods at stable temperatures in a heat-insulated container in which the resident ideal temperature results in a temperature which is greater than that of the freezing temperature of water. Therefore, the blood plasma to be stored in such a device would be held at a temperature which is elevated compared to the instant invention.

The patent to Faust, et al. teaches the use of a cryogenically frozen package article in which two plates are adapted to rotate about a common line of registry so that a pouch containing blood plasma is sandwiched therebetween. There is no integral cryogenic liquid associated therewith, and therefore does not provide an eutectic liquid as does applicant for the beneficial remote cooling according to the instant invention.

The remaining citations show the state of the art further and diverge even more from the claimed inventive nexus as described infra.

SUMMARY OF THE INVENTION

By way of contrast, the instant invention describes and claims an instrumentality which allows blood banks to obtain the highest value for the plasma they collect by plasmapheresis at remote donor sites located some distance from their main freezing facilities. The instant invention avoids the expense and difficulties associated with the prior art devices by freezing plasma at the situ of collection and freezing the plasma as effectively as had the plasma been frozen at the main freezing facility.

The device at the same time stores the frozen plasma adequately until it is delivered to the main center, which typically may be several hours later. By virtue of the apparatus according to the instant invention, blood banks will be able to access new areas heretofore logistically impractical or to expand their existing mobile operations.

In essence, the apparatus according to the present invention is a portable freezer that does not have any onboard integral refrigeration compressors or the like associated therewith. Rather it acts like a "battery" in that it is "recharged" overnight by placement in a $-30°$ C. walk-in or chest freezer. The device is specially constructed to retain this extremely cold temperature for protracted periods of time, and its ability to maintain coldness is enhanced by placement in a specially configured insulated transport case.

Collectively, the freezer and thermal transport device according to the instant invention are taken to a donor site to freeze a multiplicity of pouches of plasmapheresed plasma during a normal working regimen. The device is configured such that temperature rise during the course of a normal working day is only approximately $3°$ C. until it is returned back to the primary blood storage facility for "recharging" the device at the end of the working day. The design of the freezer allows it to store frozen plasma and to freeze plasma into a frozen state with sufficient thermal over-design to serve as a reliable transport device with a safety factor against heat predations engineered therein.

OBJECTS OF THE INVENTION

Accordingly, it is the primary object of the instant invention to provide a novel and useful plasma storage freezer and thermal transport device therefore.

A further object of the present invention is to provide a device of the character described above which is extremely safe to use and results in storing blood plasma at its highest, most vibrant state.

A further object of the present invention contemplates providing a device as characterized above which is relatively inexpensive to manufacture making it both attractive for use as an alternative to prior-existing techniques and extremely transportable to facilitate its deployment into relatively inaccessible areas.

A further object of the present invention is to provide a device as characterized above which is extremely durable in construction, reliable in operation and which has the capability of maintaining extremely low temperatures for extended periods of time.

A further object of the present invention is to provide a device as characterized above which is extremely effective in lowering the temperature of blood plasma rapidly to preserve its quality.

Viewed from one vantage point, it is an object of the present invention to provide a cryogenic freezer and a transport device which preserves blood plasma. The transport device has a hollow interior surrounded by insulation, a plurality of castors on a bottom surface of the transport, and means to access the hollow interior. A cryogenic freezer is removably disposed within the hollow interior. The freezer has a eutectic fluid surrounded by heat conductive walls which extract heat from the blood plasma. Means to place the blood plasma in heat exchange relationship with the cryogenic freezer to freeze the blood plasma are provided.

Viewed from a second vantage point, it is an object of the present invention to provide a freezer and transport device to preserve thermolabile fluids from temperature degradation. It includes a freezer having a plurality of adjacent heat sinks each having heat-conductive walls with at least two of the conductive walls from two adjacent heat sinks oriented in face-to-face registry such that a void exists between the two conductive walls of the adjacent heat sinks. Means to access the void between the adjacent heat sinks is provided such that the void receives a pouch or pouches within which the thermolabile fluid is disposed. The heat sinks extract heat from the fluids. The transport device includes insulative material and means to receive the freezer within a hollow formed within the insulative material of the transport device. Means to facilitate translation of the transport device are also included.

Viewed from a third vantage point, it is an object of the present invention to provide a method for preserving the vitality of thermolabile products, the steps including: providing a heat sink with an eutectic fluid, freezing the eutectic fluid in a powered freezer, insulating the heat sink, transporting the heat sink to a remote site for receiving the thermolabile product, freezing the thermolabile product by contact with the heat sink, returning the heat sink to a powered freezer, including removing the thermolabile product and refreezing the eutectic fluid with the powered freezer for subsequent reuse.

Viewed from a fourth vantage point, it is an object of the present invention to provide a cryogenic freezer for protecting a thermolabile product from degradation, including a heat sink having an internal eutectic fluid maintained at a low temperature with respect to the thermolabile product so as to freeze the product quickly upon contact therewith, and a void integrally formed in the freezer to receive the thermolabile product therewithin for freezing.

These and other objects will be made manifest when considering the following detailed specification when taken in conjunction with the appended drawing figures.

BRIEF DESCRIPTION OF PREFERRED EMBODIMENTS

Figure 1:
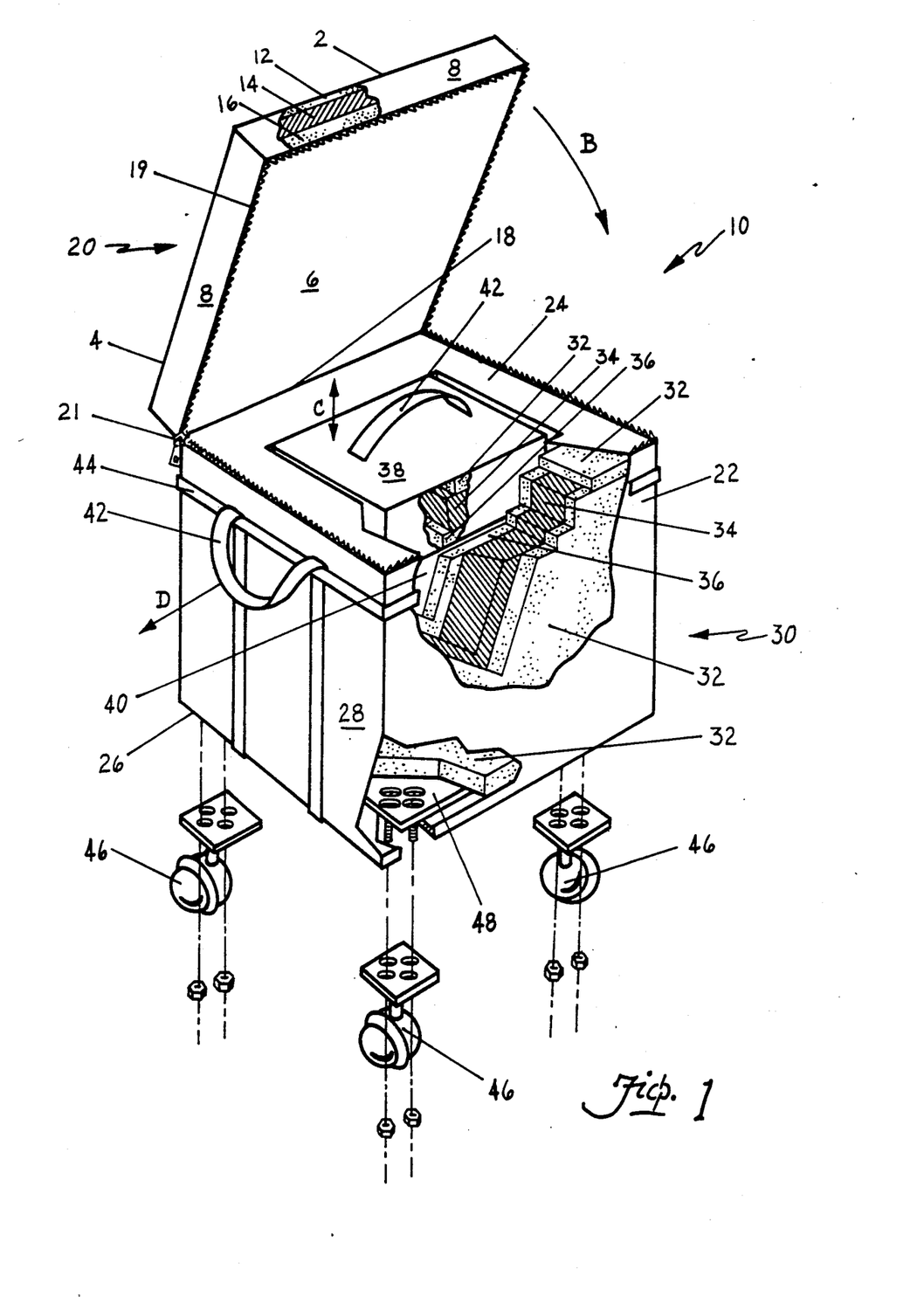
FIG. 1 is a perspective view of the transport device according to the present invention showing a hollow area at a central-most portion thereof.
Figure 2:
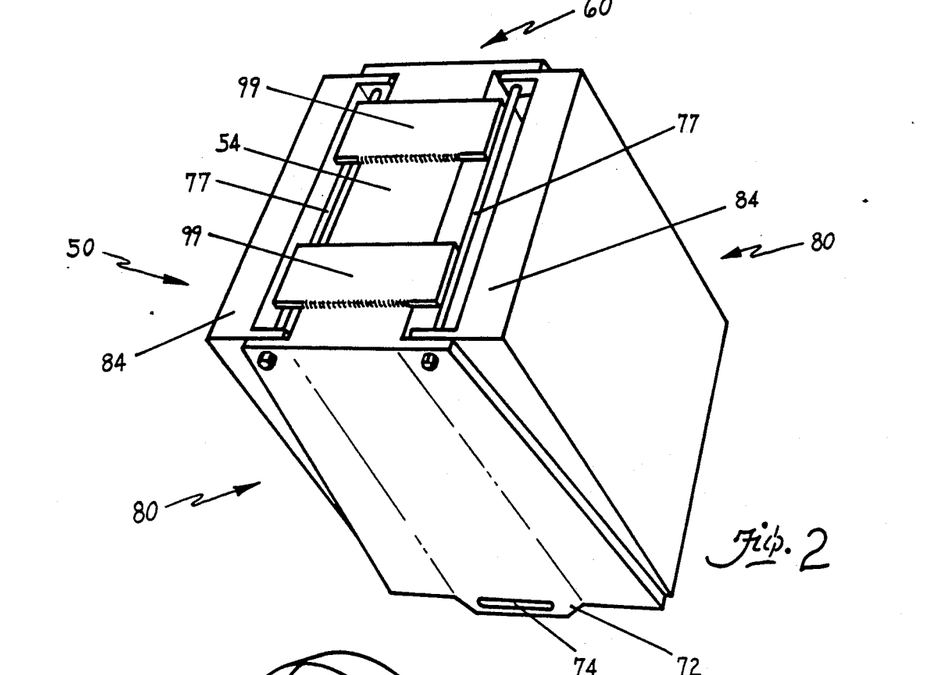
FIG. 2 is a rear perspective view of the plasma freezer storage device according to the present invention configured to fit within the hollow of the transport device shown in FIG. 1.
Figure 3:
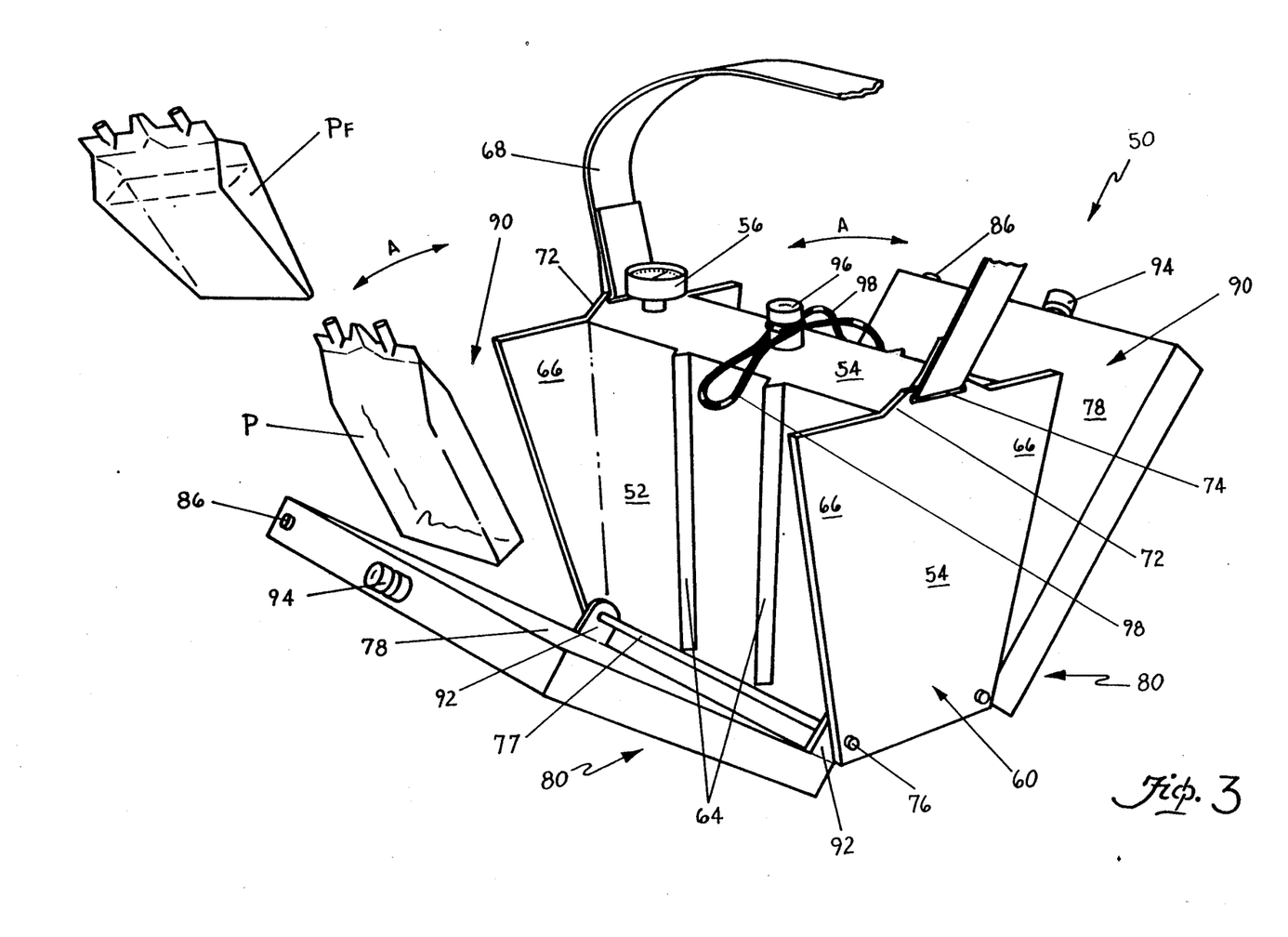
FIG. 3 shows the plasma storage freezer according to the present invention in an open, deployed configuration, preparatory to receiving a pouch "P" of blood plasma therewithin.
Figure 4:
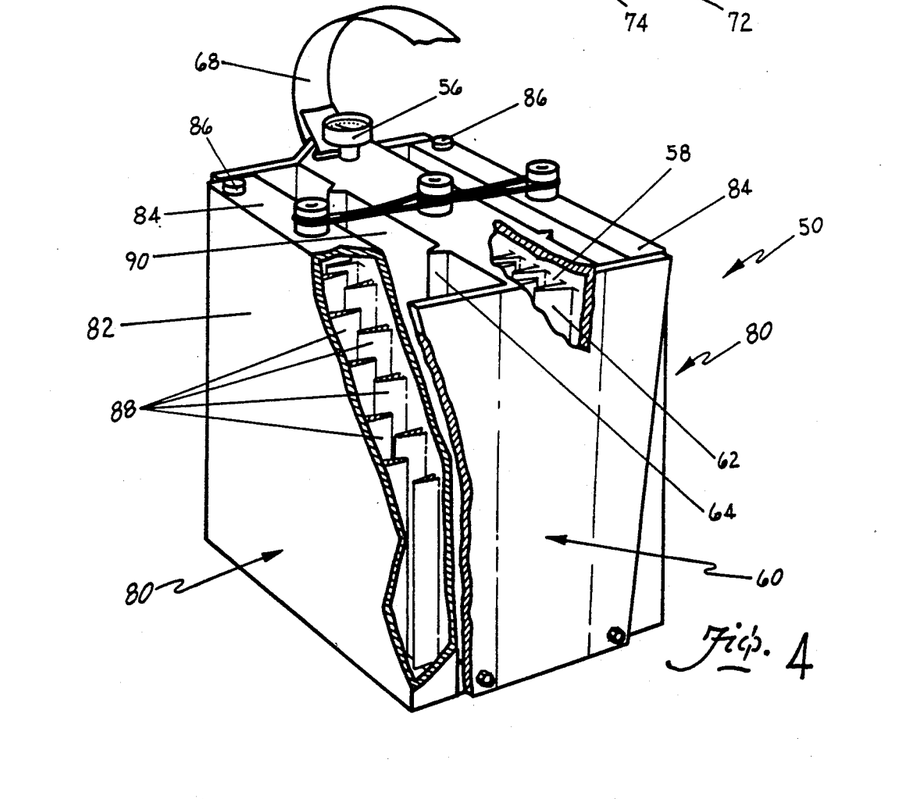
FIG. 4 is a view similar to FIG. 3 in perspective with portions fragmented away for clarity showing the plasma storage freezer in a closed position, suitable for placement within the thermal transport device of FIG. 1.

Referring to the drawings now, wherein like numerals denote like parts throughout the various drawing figures, numeral 10 of FIG. 1 is directed to the thermal transport device according to the present invention, and numeral 50 of FIGS. 2 through 4 is directed to a plasma storage freezer to be described.

In its essence, the plasma storage freezer 50 has an exterior dimension complemental to a hollow 40 formed within the thermal transport device 10. Thus, the freezer 50 can be placed within the transport device 10 and maintain its cold temperature for protracted periods of time. The transport device 10 includes a lid 20 which seals a compartment 30. In turn, the compartment 30 cooperates with a plug 38 which when removed, exposes the hollow 40. The plasma storage freezer 50 freezes plasma pouches "P" and is placed within the transport device 10. The freezer 50 itself (FIGS. 3 and 4) includes a central heat sink 60 of a boxlike configuration, which is flanked on two sides thereof by lateral heat sinks 80. The lateral heat sinks 80 are adapted to move along the direction of the arrows "A" exposing a plasma receiving void for receiving pouches of plasma "P" between the central heat sink 50, and each of the lateral heat sinks 80.

More particularly, and with respect to FIG. 1, the transport device 10 includes a lid 20 having an exterior skin 2 preferably formed from canvas. The canvas skin 2 is configured to define a top surface 4, a bottom surface 6 and peripheral side walls 8 to define a substantially rectangular cross-section construct. An interior of the lid 20 is formed from material defining an insulative core. More specifically, a laminate is provided having a rubber outer layer 12, a rubber inner layer 16 which collectively sandwich a foam central layer 14. The rubber layers 12, 16 can be of the type defined as a closed cell elastomer and the central layer can be formed from polyurethane. Collectively, the laminated insulative core provides an R value of approximately 32. A hinge 18 appears along a lower edge at the confluence of the bottom surface 6 and a rear peripheral side wall 8 which connects the lid 20 to a compartment 30. One-half of a zipper 19 circumscribes the bottom surface 6 on three sides, apart from the hinge 18 for connection with the compartment 30.

The compartment 30 has a top panel 24 which, at its outer periphery, that is, at the juncture with its peripheral downwardly depending side panels 28, has a zipper 21 which is complemental to the zipper 19 on the lid 20. Thus, the lid 20 can be sealed to the compartment 30. The lid 20 moves in the direction of the arrow "B" for closure with respect to the compartment 30.

The compartment 30 also is formed from an outer rubber layer 32, an inner rubber layer 36, and a central foam layer 34, similar to the lid 20. It is encased in a canvas skin 22. This laminate provides a high R value, typically 32.

The top panel 24 includes a rectangular opening within which a plug 38 is fitted. The plug 38 is similarly provided with the outer rubber layer 32, central foam layer 34 and inner rubber layer 36. In addition, the plug 38 includes a handle 42 to facilitate removal of the plug 38 along the direction of the arrow "C". The plug 38 when removed exposes an interior hollow 40 which is dimensioned to receive the plasma storage freezer 50 to be discussed.

In addition to the handle 42 provided on the plug 38, a further pair of handles 42 are disposed on the outer exterior canvas skin 22 to facilitate in translating the thermal transport device 10 as suggested by the arrow "D". More specifically, the one, shown handle 42 is formed from a elongate ribbon of material having two parallel portions which extend downwardly and under the compartment 30, underlying the bottom panel 26. A free looped end 42 defining the handle is reinforced by a circumscribing band 44 extending around the periphery of the compartment 30 by girding the peripheral side panels 28. A companion handle 42 is provided opposite the one shown on an opposing side panel 28.

The bottom panel 26 of the compartment 30 includes a reinforcement substrate 48 preferably formed from aluminum and of somewhat rectangular configuration and having a plurality of castor receiving countersunk screws depending from corners of the rectangular base. This substrate 48 is interposed between the bottom rubber layer 32 and the canvas skin 22. A plurality of castors 46 secure to the corners on the substrate 48 by means of plates supporting the castors 46 and fastened to the countersunk screws with nuts as shown.

With respect to FIGS. 2, 3 and 4, the details with respect to the freezer 50 can be discerned. As mentioned, a central heat sink 60 cooperates with a pair of lateral heat sinks 80 on sides thereof so that when one or more pouches of plasma "P" are interposed between a lateral heat sink 80 and the central heat sink 60, the plasma can be rapidly cooled and frozen. More specifically, the central heat sink 60 is of substantially box-like configuration having a pair of major conductive walls 52 on opposed sides thereof which are circumscribed by peripheral walls 54. One top peripheral wall 54, of rectangular configuration, supports a thermometer 56 passing through the wall 54 and indicating the temperature of an interior 58 of the central heat sink 60. The side peripheral walls are isosceles trapezoidal constructs having upwardly and outwardly diverging side edges. Thus these side walls have a rectangular portion 54 and a triangular wing portion 66 welded thereto.

As shown in FIG. 4, the interior 58 includes a plurality of thermal ribs 62 disposed on interior surfaces of the major conductive walls 52. These thermal ribs 62 extend vertically and are oriented such that the ribs 62 of the opposed conductive walls 52 are interleaved so that heat transfer from the conductive wall 52 to the interior 58 is carried out most expeditiously. Note that while the ribs 62 extend inwardly towards the interior, they stop short of the opposed conductive wall 52 so that a serpentine path is provided within which the liquid contained within the central heat sink 60 will remain in fluid communication. The thermometer 56 denotes the interior temperature to determine whether or not the heat sink 60 is sufficiently cold for its intended purpose. Typically, the interior 58 will carry a brine solution such as calcium chloride so that a eutectic temperature as low as −30° C. can be created and maintained within the interior. The brine solution is placed within the interior through the same opening which receives the thermometer 56.

Outer, exposed surfaces of the conductive walls 52 both have a pair of channel-forming indicators 64 disposed on the surface of the walls 52 which run substantially vertically. The purpose of the indicators 64 is to imprint a recess on one surface of the plasma pouch "P" so that should the plasma pouch "P" be inadvertently left in a warm environment long enough to thaw, migration of the liquid plasma will disturb the channels formed in the plasma pouch "P" indicating that the temperature has reached an undesirable level, rendering the plasma suspect.

At the juncture of each of two side walls 54 and the conductive wall 52 is the wing 66 serving as a guide plate. Each guide plate 66 and side wall 54 is provided at its uppermost extremity with a support for a handle strap 68 connected to the guide plate 66 and side wall 54 by means of raised crown 72. The crown 72 attaches to the guide plate 66 and side wall 54 by means of welding or is integrally formed therewith. A slit 74 contained on the crown 72 receives the handle strap 68. In this way, the handles 68 can be collapsed to the storage position versus an upwardly extended configuration, such as that shown in FIG. 3.

In addition, the guide plates 66 include, at a lowermost portion, similar pivot pins 76 interconnected by a pivot rod 77 (FIGS. 2 and 3) which serve as a hinge connector for the lateral heat sinks 80. As shown, each lateral heat sink 80 flanks the conductive walls 52 of the central heat sink 60. Thus, each lateral heat sink 80 includes a conductor wall 78, an outer wall 82 opposite from the conductor wall 78 and circumscribing walls 84 extending around the periphery of both the conductor wall 78 and the outer wall 82. As shown in FIG. 3, the pivot rod 77 communicates with and is affixed to the lateral heat sink 80 by means of a flange 92 oriented at lower, outer borders inboard of the conductor wall 78.

Each lateral heat sink 80 includes a plug 86 disposed on a top circumscribing wall 84 allowing access to an interior thereof. Like the central heat sink 60, the lateral heat sinks 80 each include internal ribs 88 emanating from the conductor wall 78. In addition, internal ribs 88 may optionally be provided inwardly on the outer wall 82 to provide the same type of interleaving effect shown with respect to the central heat sink 60. Plug 86 is removably accessible to allow a similar brine solution to be introduced within the interior of each lateral heat sink 80.

In general, the freezer 50 is adapted to go from an open position as shown in FIG. 3 to a closed position as shown in FIG. 4 by motion of the lateral heat sinks 80 along the direction of the double-ended arrows "A" of FIG. 3. To this end, a pair of posts 94 are disposed, one on each lateral heat sink 80 on the top circumscribing wall 84 thereof. The posts 94 are oriented to communicate with a central post 96 disposed on the central heat sink 60 along its top peripheral wall 54. An elastic tether 98 defines pressure means and extends between the central post and lateral heat sink post 94 to serve as a circumscribing band keeping the lateral heat sink 80 in the closed position. Two such tethers 98 are shown.

FIG. 2 reflects that on a bottom surface of the central heat sink 60, on a bottom peripheral wall 54, the device is limited with respect to the degree to which it can be open by means of a pair of stop plates 99 welded onto the bottom peripheral wall 54 extending outwardly towards pivot rods 77. The plates 99 serve as an abutment stop which encounters the bottom circumscribing walls 84 of the lateral heat sinks 80.

As thus far described, especially in FIG. 3, a plasma receiving void 90 is provided within which the pouches of plasma "P" are adapted to be received. The void is designed so that each juncture of a lateral heat sink 80, with respect to it central heat sink 60, can accommodate two such pouches of plasma "P". Thus, four pouches "P" are adapted to be sandwiched between the central heat sink 60 and the lateral heat sinks 80, as configured. The heat conductive walls 78 and 52 close on the pouch P applying pressure to mold the pouch in a wedge shape shown as $P_f$ in FIG. 3 and defining wedge means. Thus when the lateral heat sink is closed, the walls 52 and 78 diverge upwardly and outwardly. It has been found that a wedge shaped frozen plasma pouch results both in higher "factor 8" yields and eliminates the traditional 3-4% fluid loss heretofore resulting from plasma adhering to a top portion of the pouch P. The wedge shape engenders freezing from the bottom edge of the pouch P. This minimizes precipitation of ions and proteins to a lower part of the pouch. Furthermore, the wedge shaped plasma is more easily removeable from the pouch P.

In addition, however, the dimension of the hollow 40 in FIG. 1 is such that pouches "P" once frozen, can be placed between the outer wall 82 of the freezer 50 and within the hollow 40 of the thermal transport device 10 so that an additional four pouches may be carried with a high degree of surety that they will be maintained at the proper temperature, once they have been initially frozen by placement between the lateral heat sink 80 and the central heat sink 60.

Note that the conductive wall 78 of lateral heat sink 80 is substantially flat. This allows a smooth contour heat transfer surface for the plasma. Typically, indicia is written on the plasma pouch "P" which is best preserved readable by placing the pouch label side adjacent the flat surface of the conductive wall 78.

In use and operation, the interiors of the container 50 are filled with a brine solution and placed in a commercial freezer rendering interior temperature below the eutectic temperature of the brine or approximately −30° C. The freezer 50 is formed from metal such as steel or aluminum which has been coated with a smooth surface, such as teflon, which makes it difficult for ice to stick to it. Thereafter, it is placed in the thermal transport device 10 and taken into the field to obtain and collect blood plasma. As the plasma is collected, individual pouches "P" are placed within the void 90 formed from moving the lateral heat sink 80 from a closed to an open position and interposing the plasma pouch "P" between it and its central heat sink 60. Not all pouches have the same volume of blood contained therein. Because of the wedge shape, this volumetric difference is taken into account without difficulty when two pouches are placed side by side. Extra storage is also provided between an outer conductor wall 78 and walls defining the hollow interior 40 of the thermal device 10. The wedge shape allows inverted, alternate stacking. The device 10 when conscientiously frozen and then maintained within the insulative transport device 10, will rapidly freeze the blood plasma derived from a typical day's work to maintain the blood plasma at its optimal temperature for a protracted period of time in order to preserve the quality of the plasma.

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. A freezer and transport device to preserve thermolabile fluids from temperature degradation, comprising, in combination:

said freezer having a plurality of adjacent heat sinks each having heat conductive walls with at least two said conductive walls from two said adjacent heat sinks oriented in face to face registry, such that a void exists between said two conductive walls of said adjacent heat sinks, releasable pressure means to access said void between said adjacent heat sinks such that said void receives a pouch within which the thermolabile fluid is disposed when said pressure means is relaxed and said heat sinks extract heat from the fluids by said pressure means forcing said heat sinks together, and said transport device includes insulative material and means to receive said freezer with a hollow formed within said insulative material of said transport device, and means to facilitate translation of said transport device.

2. The device of claim 1 wherein said plurality of heat sinks includes a central heat sink having a hollow interior and provided with a plurality of internal thermal ribs emanating from said conductive wall in heat conductive relation and a eutectic mixture is contained within said interior.

3. The device of claim 2 wherein said plurality of heat sinks include at least one lateral heat sink connected with pivot means to said central heat sink at a lowermost portion of each said heat sink whereby rotation of said one lateral heat sink about said pivot means opens to reveal a void to receive the thermolabile fluid.

4. A cryogenic freezer and a transport device to preserve blood plasma, comprising, in combination:
said transport device having a hollow interior surrounded by insulation,
a plurality of castors on a bottom surface of said transport device,
means to access said hollow interior,
said cryogenic freezer removably disposed within said hollow interior of said transport device,
said cryogenic freezer having an eutectic fluid and heat conductive walls to extract heat from the blood plasma,
and means to place the blood plasma in heat exchange relation between said heat conductive walls of said cryogenic freezer to freeze and preserve the blood plasma,
wherein said means to access said hollow interior includes a lid which is pivotally connected to an underlying compartment which form a portion of said transport device,
and both said lid and said compartment include insulating means to provide a high R value,
and said compartment includes an upper inner surface provided with a plug which is removable from said upper inner surface, underlies said lid, and said plug when removed reveals said hollow interior,
wherein said compartment is formed from a laminate of highly insulative material and an exterior surface of both said compartment and said lid is provided with an abrasion-resistant, exterior skin,
wherein a bottom surface of said compartment is provided which has been reinforced with a rigid substrate of substantially rectangular configuration above said skin and having a rectangular base and corners thereof from which depend a plurality of said castors for ease in moving said container,
wherein said insulation includes two layers of rubber with an interposed foam layer.

5. The device of claim 4 including pull handles on both said plug and said exterior skin of said container.

6. The device of claim 5 wherein said hollow interior of said container is slightly longer than one dimension of said freezer to admit storage of additional previously frozen blood plasma pouches between outside conductive surfaces of said freezer and said hollow interior.

7. A cryogenic freezer and a transport device to preserve blood plasma, comprising, in combination:
said transport device having a hollow interior surrounded by insulation,
a plurality of castors on a bottom surface of said transport device,
means to access said hollow interior,
said cryogenic freezer removably disposed within said hollow interior of said transport device,
said cryogenic freezer having an eutectic fluid captured within heat conductive walls to extract heat from the blood plasma,
and sandwich means to the blood plasma in heat exchange relation between adjacent heat conductive walls of said cryogenic freezer to freeze and preserve the blood plasma in a frozen wedge shape configuration.

8. The device of claim 7 wherein said means to access said hollow interior includes a lid which is pivotally connected to an underlying compartment which form a portion of said transport device,
and both said lid and said compartment include insulating means to provide a high R value,
and said compartment includes an upper inner surface provided with a plug which is removeable from said upper inner surface, underlies said lid, and said plug when removed reveals said hollow interior.

9. The device of claim 8 wherein said compartment is formed from a laminate of highly insulative material and an exterior surface of both said compartment and said lid is provided with an abrasion-resistant, exterior skin.

10. The device of claim 9 wherein a bottom surface of said compartment is provided which has been reinforced with a rigid substrate of substantially rectangular configuration above said skin and having a rectangular base and corners thereof from which depend a plurality of said castors for ease in moving said container.

11. The device of claim 10 wherein said insulation includes two layers of rubber with an interposed foam layer.

12. The device of claim 7 wherein said wedge means includes two adjacent said heat conductive walls including a pivot at one edge of each said wall, thereby allowing arcuate jaw-like closing between said adjacent heat conductive walls.

13. A freezing device for forming a wedge shaped thermolabile product, comprising, in combination:
jaw-like heat sinks which include pivot means which allow said sinks to move from an open to a closed position,
said open position allowing the product to be placed between said sinks and sandwiched therebetween in said closed position an area of the thermolabile product closer to the said pivot means is thinner than an area of the thermolabile product further from said pivot means, and further comprising an insulated, wheeled transport device circumscribing said freezing device.

14. A freezer and transport device to preserve thermolabile fluids from temperature degradation, comprising, in combination:

said freezer having a plurality of adjacent heat sinks each having heat conductive walls with at least two said conductive walls from two said adjacent heat sinks oriented in face to face registry, such that a void exists between said two conductive walls of said adjacent heat sinks, means to access said void between said adjacent heat sinks such that said void receives a pouch within which the thermolabile fluid is disposed and said heat sinks extract heat from the fluids, and said transport device includes insulative material and means to receive said freezer with a hollow formed within said insulative material of said transport device, and means to facilitate translation of said transport device, wherein said plurality of heat sinks includes a central heat sink having a hollow interior and provided with a plurality of internal thermal ribs emanating from said conductive wall in heat conductive relation and a eutectic mixture is contained within said interior, wherein said plurality of heat sinks include at least one lateral heat sink connected with pivot means to said central heat sink at a lowermost portion of each said heat sink whereby rotation of said one lateral heat sink about said pivot means opens to reveal a void to receive the thermolabile fluid.

15. The device of claim 14 wherein said one lateral heat sink includes a hollow interior provided with internal ribs emanating from said conductive wall to enhance heat dissipation from said conductive wall.

16. The device of claim 15 wherein both said heat sinks are formed from substantially planar sheet material oriented to form rectangular boxes, and said heat sinks are oriented so that major faces defining said conductive walls are placed in face to face registry about said pivot means, said pivot means supported on a pair of wing-like guide-plates formed at edges of said central heat sink, and, at a top end of said guide-plates, a strap-like handle attached to said central heat sink by means of a crown having a slit integrally formed on said crown whereby said handle collapses adjacent said central heat sink and form a low profile when not in use.

17. The device of claim 16 wherein a second lateral said heat sink is similarly configured as said one lateral heat sink but disposed on a side of said central heat sink opposite from said one lateral heat sink, and all said heat sinks are provided with an upwardly extending post extending from a top surface of each said heat sink and a pair of tethers overlies a central said post on said central heat sink which are oriented to extend over said posts disposed on said lateral heat sinks to maintain said heat sinks in closed configuration.

18. A cryogenic freezer for protecting a thermolabile product from degrading, comprising, in combination:

at least two heat sink means each having an internal eutectic fluid maintained at a low temperature with respect to the thermolabile product so as to freeze the product quickly upon contact therewith, and a void receiving means integrally formed in said freezer to receive the thermolabile produce and expose the product to the low temperature, said void receiving means formed by said two heat sink means oriented in a jaw-like configuration, including pivot means at one area of each said heat sink to allow said heat sinks to move from an open, product receiving and removing position to a closed product freezing position.

19. The freezer of claim 18 further including a pressure means forcing said two heat sink means to press against the thermolabile product to promulgate rapid cooling.

20. The freezer of claim 18 further including indicator means on one of said heat sinks, said indicator means imparting to the thermolabile product a temperature dependant telltale correlative of the thermolabile product having likely been exposed to an undesirable elevated temperature.

21. The cryogenic freezer of claim 18 including a thermal transport device superposed about said freezer including a compartment having a hollow therewithin, within which the freezer is to be deployed, a plug having insulative properties occluding an opening defined by a top of the hollow to seal the freezer therewithin, and an overlying lid occluding the plug to further deter heat migration.

22. A cryogenic freezer and a transport device to preserve blood plasma, comprising, in combination:

said transport device having a hollow interior surrounded by insulation, a plurality of castors on a bottom surface of said transport device, means to access said hollow interior, said cryogenic freezer removably disposed within said hollow interior of said transport device, said cryogenic freezer having an eutectic fluid captured within heat conductive walls to extract heat from the blood plasma, and means to place the blood plasma in heat exchange relation between said heat conductive walls of said cryogenic freezer to freeze and preserve the blood plasma, wherein said insulation includes two layers of rubber with an interposed foam layer.

23. A freezer and transport device to preserve thermolabile fluids from temperature degradation, comprising, in combination:

said freezer having a plurality of adjacent heat sinks each having heat conductive walls with at least two said conductive walls from two said adjacent heat sinks oriented in face to face registry, such that a void exists between said two conductive walls of said adjacent heat sinks, means to access said void between said adjacent heat sinks such that said void receives a pouch within which the thermolabile fluid is disposed and said heat sinks extract heat from the fluids, and said transport device includes insulative material and means to receive said freezer with a hollow formed within said insulative material of said transport device, and means to facilitate translation of said transport device, wherein said plurality of heat sinks includes a central heat sink having a hollow interior and a eutectic mixture is contained within said interior, wherein said plurality of heat sinks include at least one lateral heat sink connected with pivot means to said central heat sink at a lowermost portion of each said heat sink whereby rotation of said one lateral heat sink about said pivot means opens to reveal a void to receive the thermolabile fluid.

24. The device of claim 1 wherein said releasable pressure means includes an elastic tether which forces said sinks to intimately contact the pouch for optimal heat transfer.

* * * * *

UNITED STATES PATENT AND TRADEMARK OFFICE
CERTIFICATE OF CORRECTION

PATENT NO. : 5,103,651
DATED : April 14, 1992
INVENTOR(S) : Coelho, et al.

It is certified that error appears in the above-indentified patent and that said Letters Patent is hereby corrected as shown below:

On the title page, please insert an originally-named inventor:

--Charles Griffiths, of London, England.--

Signed and Sealed this

Fourteenth Day of November, 1995

Attest:

BRUCE LEHMAN

*Attesting Officer*  *Commissioner of Patents and Trademarks*